United States Patent
Wehrli

(10) Patent No.: US 9,498,414 B1
(45) Date of Patent: Nov. 22, 2016

(54) SYSTEM AND METHOD FOR REDUCING PLAQUE ON TEETH

(71) Applicant: Janet M. Wehrli, Omaha, NE (US)

(72) Inventor: Janet M. Wehrli, Omaha, NE (US)

(*) Notice: Subject to any disclaimer, the term of this patent is extended or adjusted under 35 U.S.C. 154(b) by 0 days.

(21) Appl. No.: 14/121,414

(22) Filed: Sep. 3, 2014

Related U.S. Application Data

(63) Continuation-in-part of application No. 12/380,972, filed on Mar. 6, 2009, now abandoned, which is a continuation-in-part of application No. 11/505,167, filed on Aug. 16, 2006, now abandoned.

(60) Provisional application No. 60/787,145, filed on Mar. 30, 2006.

(51) Int. Cl.
| | | |
|---|---|---|
| A61K 45/06 | (2006.01) | |
| A61K 9/06 | (2006.01) | |
| A61Q 11/00 | (2006.01) | |
| A61K 8/19 | (2006.01) | |
| A61K 8/92 | (2006.01) | |

(52) U.S. Cl.
CPC ............ *A61K 8/19* (2013.01); *A61K 8/922* (2013.01); *A61K 8/925* (2013.01); *A61Q 11/00* (2013.01); *A61K 2800/40* (2013.01)

(58) Field of Classification Search
CPC .... A61K 2300/00; A61K 47/44; A61K 9/06; A61Q 11/00
See application file for complete search history.

(56) References Cited

U.S. PATENT DOCUMENTS

| | | | |
|---|---|---|---|
| 4,148,872 A | 4/1979 | Wagenknecht et al. | 424/48 |
| 4,150,112 A | 4/1979 | Wagenknecht et al. | 424/48 |
| 4,156,715 A | 5/1979 | Wagenknecht et al. | 424/48 |
| 4,157,385 A | 6/1979 | Wagenknecht et al. | 424/48 |
| 4,159,315 A | 6/1979 | Wagenknecht et al. | 424/48 |
| 4,161,517 A | 7/1979 | Wagenknecht et al. | 424/48 |
| 4,225,579 A | 9/1980 | Kleinberg | 424/48 |
| 4,229,485 A | 10/1980 | Brown et al. | 426/305 |
| H83 H | 7/1986 | Poletto et al. | 424/49 |
| 5,249,570 A | 10/1993 | Cox | 128/206.28 |
| 5,405,836 A | 4/1995 | Richar et al. | 514/23 |
| 5,455,024 A | 10/1995 | Winston et al. | 424/52 |
| 5,693,334 A | 12/1997 | Miskewitz | 424/440 |
| 5,944,516 A | 8/1999 | Deshaies | 433/1 |
| 5,993,786 A | 11/1999 | Chow et al. | 424/49 |
| 6,014,950 A | 1/2000 | Rogers | 119/710 |
| 6,050,224 A | 4/2000 | Owens | 119/710 |
| 6,238,648 B1 * | 5/2001 | Leusch | A61K 8/345 424/49 |
| 6,309,676 B1 | 10/2001 | Lewandowski | 424/754 |
| 6,405,681 B1 | 6/2002 | Ward | 119/707 |
| 6,509,007 B2 | 1/2003 | Rajaiah et al. | 424/53 |
| 6,610,276 B2 | 8/2003 | Melman | 424/57 |
| 6,649,147 B1 | 11/2003 | Ye et al. | 424/49 |
| 6,669,928 B1 | 12/2003 | Gurol | 424/49 |
| 6,685,971 B2 | 2/2004 | Xu | 424/725 |
| 6,827,041 B2 | 12/2004 | Hague et al. | 119/709 |
| 6,886,497 B1 | 5/2005 | Hague | 119/710 |
| 6,905,673 B2 | 6/2005 | Rajaiah et al. | 424/49 |
| 6,997,708 B2 | 2/2006 | Allred et al. | 433/80 |
| 7,013,838 B2 | 3/2006 | Hague | 119/710 |
| 7,022,314 B2 | 4/2006 | Barabolak et al. | 424/48 |
| 2003/0113276 A1 * | 6/2003 | Rajaiah et al. | 424/49 |
| 2003/0124230 A1 | 7/2003 | Zielinski | |
| 2003/0175326 A1 | 9/2003 | Thombre | 424/442 |
| 2003/0206948 A1 | 11/2003 | Gergely et al. | 424/465 |
| 2004/0057910 A1 * | 3/2004 | Lee et al. | 424/53 |
| 2004/0101493 A1 | 5/2004 | Scott et al. | 424/49 |
| 2004/0101494 A1 | 5/2004 | Scott et al. | |
| 2004/0118360 A1 | 6/2004 | Hague et al. | |
| 2004/0120900 A1 * | 6/2004 | Arsenault | A61K 8/66 424/50 |
| 2004/0244720 A1 | 12/2004 | Jia | |
| 2005/0008584 A1 | 1/2005 | Montgomery | |
| 2005/0071927 A1 | 4/2005 | Hague et al. | |
| 2005/0106111 A1 * | 5/2005 | Castor | A61Q 11/00 424/49 |
| 2005/0152851 A1 | 7/2005 | Kaminski | |
| 2005/0260544 A1 * | 11/2005 | Jones et al. | 433/217.1 |
| 2006/0088482 A1 | 4/2006 | Wulknitz et al. | |
| 2006/0239938 A1 * | 10/2006 | Perechocky | A61K 8/21 424/49 |
| 2006/0286044 A1 * | 12/2006 | Robinson et al. | 424/49 |

OTHER PUBLICATIONS

Bisla, Sharan. Dental Caries. Jul. 24, 2003. <http://sciweb.hfcc.net/biology/jacobs/micro/caries/caries.htm>.*
Merial, Oravet "Plaque Prevention is Key . . . ".
Waters, David. Tooth Wear. Waters Orthodontics. Retrieved on May 19, 2014. pp. 1-2.

* cited by examiner

*Primary Examiner* — Frederick Krass
*Assistant Examiner* — Tracy Liu
(74) *Attorney, Agent, or Firm* — James D. Welch

(57) ABSTRACT

A system and method which enables application of a composition of matter to teeth (and gums), which composition of matter remains in contact with, and adheres to, said teeth and gums for a period long enough to neutralize acids in dental plaque biofilm, inhibit plaque from adhering to teeth and gums, encourage removal of dental plaque, and form a barrier between the teeth and gums and the oral environment.

28 Claims, 2 Drawing Sheets

SYSTEM AND METHOD FOR REDUCING PLAQUE ON TEETH

This Application is a CIP of Co-Pending application Ser. No. 12/380,972, Filed Mar. 6, 2009, which was a CIP of Ser. No. 11/505,167 Filed Aug. 16, 2006, and there via Claims Benefit of Provisional Application No. 60/787,145 Filed Mar. 30, 2006.

TECHNICAL FIELD

This invention relates to means for controlling plaque on teeth, and more particularly to a method involving application of a composition of material to teeth and gums.

BACKGROUND

In humans it is known that benefits are associated with personal cleansing of teeth, and gums, after eating. For instance, brushing can remove acid containing plaque which promotes tooth decay and breath odor. However, brushing is often not possible and many people substitute chewing gum and the like. While chewing gum and the like does provide benefit, such does not neutralize teeth, and gum tissue degrading acids for a prolonged period. Even gums which contain alkaline materials, (ie. sodium bicarbonate), fail to beneficially increase the pH in an oral cavity for a prolonged period, as saliva flow dilutes and dissolves it and then it is quickly swallowed. Therefore present invention specifically does not teach use of chewing gum. It is noted that a neutral pH of 7.0, or at least a pH above about 6 is desirable where the goal is prevention of formation, or reduction in already formed existing plaque.

In animals, (eg. dogs and cats), the above recited approaches of cleaning teeth, (ie. brushing and gum chewing), are not usually convenient or even possible to practice, and approaches to controlling teeth cleanliness and preventing associated pet breath odor usually take the form of providing treated foods or mechanically abrasive chewing systems. Improved methodology of cleaning animal mouths to promote plaque removal and freshened breath thereof would provide utility.

A Search of Patents provided:
- U.S. Pat. No. 6,309,676 to Lewandowski describes a Pet Breath Ameliorator involving coating the pets food with pure natural garlic.
- U.S. Pat. No. 6,050,224 to Owens describes a Therapeutic Chew Device for Cleaning Teeth and Breath of Dogs. Said device comprises a plurality of polyester yarns with knots near opposite a rope made of rawhide impregnated with activated charcoal. The later component serves to freshen a dogs breath as it chews the device.
- U.S. Pat. No. 5,405,836 to Richard et al. describes Pet Foods such as biscuits, which contain Water Soluable Zinc Compound Coating for Controlling Malodorous Breath.
- U.S. Pat. No. 5,944,516 to Deshaies describes an Animal Tooth Cleaning Device and Method. The Device comprises a core element having a plurality of brushes extending therefrom which protrude as an animal chews it.
- U.S. Pat. No. 6,014,950 to Rogers describes a rolled or folded Terry cloth Dog Teething Toy which can be saturated with water and frozen.
- U.S. Pat. No. 5,249,570 to Cox describes an Equine/Canine Hemoglobin-Oxygen Training Mask.

Patents and Published Application to and by Hague which describe Bleached Expanded Pigskin and Products such as Animal Chews are:
- U.S. Pat. No. 6,827,041;
- U.S. Pat. No. 6,886,497;
- U.S. Pat. No. 7,013,838;
- US2004/0118360; and
- US2005/0071927.

Patents which describe antiplaque compositions and the like are:
- Patent No. H83 to Poletto et al. describes dental antiplaque agents and inhibitors of connective tissue disease.
- U.S. Pat. No. 6,669,928 to Gurol describes a peridontal composition, which can be a glycerin-free stable gel or paste capable of withstanding high pH environments without degradation.
- U.S. Pat. Nos. 4,159,315; 4,157,385; 4,156,715; 4,150,112 and 4,148,872 to Wagenknecht, deceased et al. describe plaque inhibiting composition and method in the form of chewing gum.
- U.S. Pat. No. 6,610,276 to Melman describes multi-functional dental composition containing acetic acid for preventing dental plaque, including application to animal teeth.
- U.S. Pat. Nos. 6,509,007 and 6,905,673 to Rajaiah et al. describe oral care kits and compositions containing polybutene.
- U.S. Pat. No. 5,693,334 to Miskewitz describes chewing gum product comprising gum with encapsulated sodium bicarbonate, a peroxide compound, a bulk sweetener and a flavorant, with dental health benefits.
- U.S. Pat. No. 5,455,024 to Winston et al. describes dentifrices containing zinc oxide particles and sodium bicarbonate.
- U.S. Pat. No. 7,022,314 to Barabolak et al. describes anti-plaque emulsions comprising surfactant, emulsifier and triclosan, and products containing same.
- U.S. Pat. No. 6,649,147 to Ye et al. describes a delivery system for oral care compositions comprising organosiloxane resins using a removable backing strip and methods of their use.
- U.S. Pat. No. 6,997,708 to Allred et al. describes treatment compositions and strips having a solid adhesive layer and treatment gel adjacent thereto.
- U.S. Pat. No. 4,225,579 to Kleinberg describes means and method for improving defenses against caries.
- U.S. Pat. No. 5,993,786 to Chow et al. describes anti-carious chewing gums, gels, toothpastes and dentifrices.
- U.S. Pat. No. 6,685,971 to Xu et al. describes a method and composition, which can contain an edible wax, for repairing and promoting regeneration of mucosal tissue in the gastrointestinal tract.
- Published Application No. 2006/0088482 by Wulknitz et al. describes an oral and dental agent.
- Published Application No. 2004/0101493 by Scott et al. describes chewable solid unit dosage forms and methods for delivery of active agents into occlusal surfaces of teeth. This Published Application also describes use of surfactants which decrease adherence of a composition to teeth and gums.
- Published Application No. 2005/0008584 by Montgomery is disclosed as it was identified by the Examiner in prosecuting Parent application Ser. No. 11/505,167 and describes application of sodium percarbonate in an oral composition. Montgomery 584, it is focused on teeth whitening. While whiter teeth is a side effect of the present invention, that is not the focus thereof. The present invention has as a primary focus the reducing plaque on mammalian teeth.

U.S. Pat. No. 4,229,486 to U.S. Pat. No. 4,229,485 to Brown as it was identified by the Examiner in prosecuting Parent application Ser. No. 11/505,167.

Published Application No. 2004/0244720 by Jia is disclosed as it was identified by the Examiner in prosecuting Parent application Ser. No. 11/505,167.

Published Application No. 2005/0152851 by Kaminski is disclosed as it describes a stick of semi-hard dentifrice containing sodium bicarbonate as an abrasive. This Patent describes applying a sodium bicarbonate containing semi-hard dentifrice onto to teeth, then brushing it off. As opposed to the present invention, no suggestion that the sodium bicarbonate should remain in place for a prolonged period is disclosed. Rather, the sodium bicarbonate is described as being an abrasive to aid with successful brushing.

Published Application No. 2003/0124230 by Zielinski is disclosed as it mentions reducing bad breath.

U.S. Pat. No. 6,405,681 to Ward is disclosed as it describes an animal chew toy with a reservoir for containing liquid. Further, Ward 681 discloses a Chew Toy which can dispense a dentifrice when chewed by a dog, but it does not identify other dispensing approaches.

U.S. Pat. No. 4,151,517 to Wagenknecht, deceased et al. is disclosed as it was identified by the Examiner in prosecuting Parent application Ser. No. 11/505,167.

Published Application No. 2003/02069948 by Geregly et al. is disclosed as it was identified by the Examiner in prosecuting Parent application Ser. No. 12/380,972.

Also previously identified in Examination in a Parent Application, is Published Application No. 2003/0175326 by Thombre.

It is also disclosed that Merial Inc. produces a product called "ORAVET" that comprises a polymer that is applied to pet teeth to prevent formation of plaque.

It is also known that prolonged application of sodium bicarbonate and the like to bacteria causes said bacteria to lyse, thereby rendering them unable to form plaque.

It is also known that various animals have teeth with characteristics that are genetically designed for various functions. For example, horses and cows have teeth suited for grinding whereas carniverous animals such as cats and dogs have teeth suited to ripping and tearing. An approach to inhibiting plaque formation which is applicable to all manner of teeth would therefore provide utility.

Next, please understand that what is new in the present invention is the forming of a composition of material with a pH preferably above about 7.0 that, in use, forms a barrier between teeth and gums, with respect to an oral environment, in a manner that maintains said material in contact with the teeth for a period of at least an hour. Strong acid is not involved at all!

Continuing, this CIP is filed in view of failed prior efforts in prosecution of the Parent application Ser. No. 12/380,972, in which the Examiner identified a Published Application by Lawlor, No. 2003/0103914 Published June 2003. It is believed that the Examiner's argument in that effort, to the effect that the Original Specification of the present Application did not support reciting "A method of reducing plaque on mammalian teeth that:
does not require mechanical abrasion . . . ";

was overcome in view of Page 13 of said Original 972 Specification Lines 25-32, which was very clear regarding:
the known practice of using sodium bicarbonate to abrasively remove plaque,
but that what is not known is:
"intentionally maintaining the sodium bicarbonate in contact with teeth and gum, in a substantially undiluted form, for hours and longer, before optional removal", (emphasis added).

Note: Beeswax, or the like, provides said adherent properties.

(Note, The Examiner in that prosecution withdrew the rejection based on Lawlor 914).

The foregoing identified negative limitation applies in the present invention (regarding non-use of abrasion). Further, it continued, it was believed, to avoid previously cited Melman 276 and Kamiski 230 Patents thereby avoiding their reinstatement as a basis of rejection.

As regards Lawlor, it is noted that mention of "Beeswax" therein is limited to its use in chewing gum. In that light see Page 1, in the Original Specification of the Parent 972 Application, Lines 19-28 where it clearly states:
"While chewing gum and the like does provide benefit, such does not neutralize teeth degrading acids for a prolonged period. Even gums which contain alkaline materials, (ie. sodium bicarbonate), fail to beneficially increase the pH in an oral cavity for a prolonged period, as saliva flow dilutes and dissolves it and then it is swallowed".

As a result of this identified support provided thereby a negative limitation which excludes "chewing gum" is included in Claims in this present Application, and that avoids the teachings of Lawlor. Further Lawlor does not describe using wax as a barrier between teeth and/or gums, and an oral cavity environment, let alone a barrier containing material with a pH of 7.0 or greater.

Further all Lawlor compositions are very different from the preferred present invention composition of material, which composition of material:
adheres to teeth, and gums, and serves as a barrier between teeth and gums, and the oral environment;
inhibits plaque from adhering to teeth; and
reduces and/or absorbs plaque on teeth when left in place for hours rather than minutes;
said inhibitor of plaque causing said composition of matter to present with a pH at least above 6.0 and preferably above 7.0;
and preferably comprises:
1/8 beeswax;
5/8 oil; and
2/8 plaque inhibiting material.

Again, while Lawlor does describe the use of waxes, it does not remotely suggest using them as a barrier containing material with a pH of 7.0 or greater to maintain said material in contact with teeth for repeated periods of an hour or more! Nothing in Lawlor teaches how to modify the compositions described therein to arrive at that of the preferred present invention composition of matter. In fact, Lawlor describes so many different compositions,
all of which contain *Citrus* and/or *Vitis*,
that it is difficult to understand how it provides any guidance to one skilled in the art as to which to even start with and then how to modify it to achieve the present invention composition of matter. Lawlor is in fact confusing as to what it is actually disclosing other than that it's compositions all contain *Citrus* and/or *Vitis* and that is really all that is new in Lawlor over prior art. In particular, nothing in Lawlor remotely suggests that any of its various compositions should not contain *Citrus* and/or *Vitis* acids, which the present invention specifically excludes as it seeks to neutralize acid and therefore would not add an acid to it's compositions. Again see Page 1, Lines 19-28 of the Parent 972 Application to support this, and such is definitely present in this CIP.

Further, the recitation of the present invention composition of matter forming a barrier between teeth and an oral environment is found in the Original Parent 972 Application Specification Abstract and on Page 6 Line 29.

Continuing, nothing in Lawlor remotely suggests that any of the many compositions of matter suggested therein should ever be maintained in contact with teeth for a prolonged period of an hour or more. Lawlor is focused on seconds of time and in no case does it suggest anything beyond minutes. This is probably because, as mentioned, ALL said Lawlor compositions include *Citrus* and/or *Vitis* which have a pH far below 6.0, (eg. typically 2.0-4.0), which is acidic—and again, it is well known that any material with a pH of below about 6.5, and especially below 5.5, begins to dissolve tooth enamel, which effect can become significant if contact between a low pH material and said tooth enamel is maintained over a prolonged period of an hour or more. It is therefore absolutely inconceivable that one skilled in the art would read Lawlor and conclude it should be practiced for prolonged periods of time on the order of an hour or more. Again do note, nothing in Lawlor remotely suggests that *Citrus* and/or *Vitis* should be removed from its formulations. Adding a buffering agent, it might be argued, is disclosed in Lawlor and that could allow achieving a pH above 7.0. However, Lawlor is focused on destruction of bacteria, (Anti Bacterial seed), and buffering *Citrus* and/or *Vitis* acid inhibits that capability and thus the very thing that is new in Lawlor—that is, the bacteria killing effect of *Citrus* and/or *Vitis* acids, would be nullified. Even though buffering agents can in general be applied to achieve a pH in a range of about 3 up to 10, (which well known fact Lawlor does recite), any buffering Lawlor would suggest, in a practical sense, would not be used to achieve a pH above 7.0 as that would negate achieving the result desired in the Lawlor reference, said effect being that *Citrus* and/or *Vitis* kill bacteria which Lawlor says is the previously unreported basis of the invention disclosed therein. Specifically, in Paragraph (0013) in Lawlor it states that its anti-plaque action is based on its *Citrus* and/or *Vitis* (acid) extracts disrupting bacteria membranes, thereby making bacteria more susceptible to anti-plaque agents. This is not at all remotely the basis upon which the present invention works as it does not utilize acid in it's composition! It seeks to neutralize all acids!

In this light note that the present invention, again does not contain, or even suggest that *Citrus* and/or *Vitis*, or any other acid be present. Again, the present invention seeks to neutralize acid so any said neutralized acid will not have contact with teeth over the prolonged period called for in the present invention.

And note that on Page 1 of the Original 972 Specification, beginning in Line 25 it recites:

"It is noted that a neutral pH of 7.0, or at least a pH above about 6 is desirable where the goal is prevention of formation, or reduction in already formed existing plaque".

(Also note that plaque by nature produces an acid environment well below 5.5). That, again, distinguishes over Lawlor as, again, Lawlor does not suggest removal of *Citrus* and/or *Vitis* acid from its formulations. Lawlor could provide a buffered pH over 7.0, but that would inhibit the bacteria killing action of the *Citrus* and/or *Vitis* acid, which is the primary focus therein. One skilled in the art would simply not be led to increase pH in a Lawlor composition as that would decrease the effectiveness of the Lawlor invention. Continuing, a negative limitation could be added to the Claims that identifies *Citrus* and/or *Vitis* are specifically not present, but the Present Invention Original Specification does not specifically support such. Note, it is specifically stated here that the present invention does not comprise *Citrus* and/or *Vitis*. It simply was not thought to directly address the absence of *Citrus* and/or *Vitis* acid in the present invention composition when writing the Original Parent 972 Specification, as the present invention is not focused on killing bacteria with low pH compositions, but rather on controlling plaque formation with high pH values, such as provided by the Sodium or Potassium Bicarbonates. (Again see Original Specification Page 1, Lines 25-28 where it says such plaque control requires a pH above about 6.0). In general there are an infinite number of things that are not part of the present invention that are not mentioned in the Specification, as is always the case in Patent Applications.

Further it is stated in the Original Parent 972 Specification that Sodium and/or Potassium Bicarbonate or the like are a part of the Composition of Matter—and such provides a basic pH of above 7.0. In that light, and in view of the fact that no acidic components were recited as required in the present invention Composition of Matter, it is believed that it should be sufficient to recite supported language to the effect that said inhibitor of plaque causes said composition of matter to present with a pH preferably above 6.0 to 7.0", and thus distinguish over Lawlor. And again, this distinguishes over Lawlor as nothing in Lawlor suggests that the *Citrus* and/or *Vitis* should be removed from it's composition, or on a practical basis that buffering agents should be included in the Lawlor compositions to increase their pH above 6.0-7.0. One skilled the art having Lawlor before him or her would not be guided thereby to delete the Critic and/or *Vitis* acids or drastically increase pH in any of its many compositions, as that would defeat the purpose of the Lawlor Published Application purposes of provided low pH compositions that kill bacteria.

Attention is also directed to the FIGS. 1 and 2, and to Page 16 in the Original Parent 972 Specification in which it is stated that "Note that FIG. 2 shows that plaque present on the dog's teeth in FIG. 1 is reduced."

The word "reduced", as it refers to plaque refers to the point that:

as a result of the sodium and/or potassium bicarbonate inhibiting plaque from adhering to teeth; and reduces and/or absorbs plaque when left in place for at least one hour;

and in conjunction with the many other distinctions with respect to Lawlor, it is now believed that the Present Invention is clearly shown to be New, Novel and Non-Obvious in view of all known references. Again, nothing in Lawlor describes a plaque reducing composition be maintained as a barrier between teeth and gums, and an oral environment for at least an hour. It is also mentioned that the Examiner's point in the earlier prosecution, regarding "at least an hour" being covered by "at least 30 seconds" was well taken, and technically, without more, has some merit. However, as argued earlier herein, no-one skilled in the art would intentionally place a *Citrus* and/or *Vitis* containing composition in contact with tooth enamel for such prolonged periods, as it would attack and act to dissolve said tooth enamel. Lawlor even alludes to this in Paragraph (0019) thereof, wherein he indicates acids can damage teeth. But even in view of that adverse affect Lawlor does not teach excluding (*Citrus* and/or *Vitis*) acid from its compositions, as does the present invention. The present invention teaches that one should not include, and should neutralize acids that might be present. Quite the opposite of what Lawlor teaches. While the teachings of Lawlor might indicate a way to control plaque on teeth, it would occur on a very different basis than does the present invention teach, (perhaps more by preventing it's formation via killing bacteria than by reducing existing plaque). Again, the present invention does not include use of a *Citrus* and/or *Vitis*, (or any other), acid containing low pH (eg. below 6.0) composition, but rather provides a composition with a pH above at least 6.0 and preferably 7.0 or above, and it is in a material that adheres to teeth and serves as a barrier between teeth and gums, and the oral environment. Such a method involving formation of a barrier containing material with a pH of 6.0-7.0 or above, between teeth and an oral environment, which barrier stays in place for at least an hour, is not remotely taught or suggested in Lawlor. Rather Lawlor suggests something like "swishing" a low pH composition around in an oral cavity for time periods on the order of seconds or at most a few minutes. And again, if a low pH material were to repeatedly remain in contact with teeth for more than a few minutes, serious damage to teeth would eventually result. One skilled in the art would not be led to do so and Lawlor does not suggest it should be done.

And for emphasis, again, nothing in Lawlor suggests removing *Citrus* and/or *Vitis* from any of its many compositions and nothing in Lawlor would lead one skilled in the art to arrive at a present invention composition which provides a composition with a pH of at least 6.0 and preferably above 7.0 and that adheres to teeth in a manner so as to repeatedly maintain said composition in contact with teeth for at least an hour or more. One skilled in the art would not be guided to remove the *Citrus* and/or *Vitis* acid from the Lawlor composition, hence, would not arrive at a present invention composition with having a pH above 7.0. Lawlor's teachings might lead one skilled in the art to buffer a Lawlor composition or otherwise keep acid levels low, but it is noted that negates the affects which are new and basic to the Lawlor invention! Lawlor compositions work by adversely affecting bacteria cell walls and making them more susceptible to anti-plaque agents. If a Lawlor composition were buffered to a pH of 7.0 or above it is believed a Citrate salt would form and the Lawlor effect would be completely lost.

It is also noted that while the present invention composition of matter does not require an acid component as does Lawlor, the original Specification does support a pH of 6.0. This might seem to be a contradiction, however, do realize that components, when present, can be weakly acidic, as compared to the strongly acidic *Citrus* and/or *Vitis* components in Lawlor. That is the reason a below 7.0 pH is recited.

And finally—to really drive home that fact that Lawlor could not possibly obviate the present invention—do note that the word "barrier" does not appear in Lawlor's Application anywhere. And, forming a barrier between teeth and gums, and an oral environment, which barrier keeps a material which does not require a strongly acidic pH material component, in contact with teeth over prolonged periods is a critical, and an absolutely distinguishing element of the present invention, over Lawlor!

Next, as it was also cited in prosecution of the Parent 972 Application, it is further believed that Melman 276 is not a particularly relevant reference compared to the present invention, as Melman 276 discloses the presence of acetic or citric acid in the formulation of its disclosed dental compositions and does not suggest excluding said components. It is noted that the present invention does not include acetic or citric acid in its composition of matter, and it is strongly emphasized that since the present invention requires that its composition of material remain in contact with mammalian teeth for a prolonged period, such as acetic or citric acid would not be at all desirable. This is because it would, over time, destroy the teeth because enamel dissolves at a PH of 5.5, which an acid would cause. In this light it is emphasized that nothing in Melman 247 would lead one skilled in the art to eliminate the acetic or citric acid and replace it with sodium or potassium bicarbonate. Those teachings are missing in Melman 247. It is also noted that Melman suggests using Hexametaphosphate in Paragraph (0016), (much like Melman 276 should be required to do to obviate present invention elements, but doesn't). It is noted that Hexametaphosphate chemical binds to Calcium and prevents natural recalcification of teeth. One skilled in the art would not know to avoid this based on Melman 276. The Examiner also, in effect, argued that the present invention limitation that the present invention composition of matter remain in place for a period of time, in a substantially undiluted form, which is sufficient to reduce plaque on the teeth thereof, is obviated by the consideration that some of the Melman paste would adhere to teeth. But again, Melman 276 provides for the presence of acetic or citric acid in the formulation of its disclosed dental compositions and does not suggest excluding said components. That being the case, one skilled in the art would not leave said acid containing composition in place for hours rather than minutes regardless of a technical interpretation of language.

Continuing, as the Claims herein are substantially Amended over the original Claims in the Parent 972 Application, it is believed the Examiner's specific 103 arguments in prosecution of Parent Applications are no longer applicable. However, under the Section 103 position of the Examiner in the prior Action, it is noted that the Examiner did identified various elements of the present invention which are variously distributed in many different references, and then argued that because the elements, in forms somehow similar to elements in the present invention exist, it would be obvious to one skilled in the art to be able to find the somehow similar elements, while not electing other unnecessary elements in said identified prior art, then modify the selected elements and appropriately combine them to arrive at the present invention. This approach can be applied to any invention. Applicant, however, finds no instructions in any single reference that would guide one skilled in the art acting as a technician rather than an inventor to arrive at the present invention. Even in view of the KSR case, Graham v. John Deere is still good law, and under it there must be teachings in one reference that would guide one skilled in the art to arrive at the new invention, which, again, Applicant does not find in any cited single reference.

As regards Kaminiski 851, it is noted that the use of sodium bicarbonate therein is as an abrasive during brushing. This reference does not lead one skilled in the art to attempt to maintain sodium bicarbonate in contact with teeth and gums for a period of time, in a substantially undiluted form, which is sufficient to reduce formation of, and remove plaque on teeth and gums. Further, the present invention calls for a larger presence of sodium or potassium bicarbonate in a material provided to cause adherence to teeth in the present invention, (eg. beeswax), than would be suggested to one skilled in the art by Kaminiski 851. It must be appreciated that sodium bicarbonate has many characteristics and properties, but the present invention does not require use of it as an abrasive.

As regards the Publication Application by Zielinski 230, it is noted that there is no mention of sodium bicarbonate therein, making it of dubious value as a valid reference. This reference teaches a food product that is meant to detoxify the liver of dogs. Again, this reference seems to be a bit far afield from the use of the present invention and was apparently used by the Examiner only to show that bad breath in dogs can be treated. However, its approach to doing so has nothing to do with the present invention use of sodium or potassium bicarbonate in a material composition that adheres to teeth and gums. Importantly, note, Zielinski 230 teaches a systemic approach, and not a topical approach as does the present invention.

Ward 681 discloses a Chew Toy which can dispense a dentifrice when chewed by a dog, but it does not identify other dispensing approaches.

As regards Montgomery 584, it is focused on teeth whitening. While whiter teeth is a side effect of the present invention, that is not the focus thereof. The present invention has as a primary focus the reducing plaque on mammalian teeth.

The use of Thorpe 777 F.2d 695, 227 USPQ 964 966 (Fed. Cir. 1985) in previous prosecution of Parent Applications is felt to now be moot in view of the Amendments to Claims presented herein.

In the prior prosecution of the Parent 972 Application, the Examiner's attention was directed to Page 13, Lines 19-25, in the Parent 972 Application, where it states:

Further, while actually counter to the focus of present invention, said method can further comprise, after some relatively long time period, (eg. hours as opposed to minutes), after application of said material to teeth and/or gums, the step of removing said material applied to said teeth and/or by an approach that results in removal of plaque removed from teeth along therewith.

to provide priority support for maintaining present invention composition of matter in contact with teeth for a prolonged period, (eg. hours rather than minutes).

It is also noted that Published Application No. 2004/0101493 by Scott et al. describes chewable solid unit dosage forms and methods for delivery of active agents into occlusal surfaces of teeth. This Published Application also describes use of surfactants which decrease adherence of a composition to teeth and gums. The present invention does not use surfactants.

It is to be noted that the Present Invention involves forming a Barrier between teeth and oral cavity for hours, (in the plural), rather than minutes. The Claims in this CIP are now focused by addition of:

said method being distinguished by the forming of, and presence of said plaque preventing and/or reducing barrier containing composition between said teeth, and gums, and said oral environment for hours rather than minutes, and the absence of any requirement for the use of chewing gum or mechanical abrasion or surfactant.

For support of the approach herein the Examiner is referred to in In re Woodruff, 919F.2nd 1575, 16 USPQ2d (Fed Cir. 1990), which provides a basis for avoiding prior art by showing said prior art teaches away from a Present Invention. Additionally, the Inventor has disclosed to me that she found it surprising to find significant concentrations of Sodium Bicarbonate present in the mouth of a subject 24 hours after application of the Present Invention composition to teeth and gums thereof. This was discovered when the Inventor had applied composition to her teeth and gums one day, and a day later noticed a "foaming" when brushing her teeth with water. Said "foaming" could only be explained by the remaining presence of composition. The inventor believes the composition had been stored in gum tissue as well as remained on teeth. It is noted that Surprising Results also are cited in re Woodruff as a method to avoid prior art!

It is to be appreciated that in this CIP chewing gum is specifically stated as not being required, but also citations that involve chewing gum, can not meet the "barrier" remaining in place criteria recited in the Pending Claims, as "chewing" gum causes removal of any barrier forming material via abrasion, (eg. by a "wiping" effect, (eg. during mastication)). Also the phrases, "does not involve chewing gum" and "does not require an acid component" are now supported in this CIP Specification.

It is also directly noted that in prior prosecution efforts, the Examiner identified an overlap between "at least two minutes" in Prior Art, and "hours rather than minutes" in the present Application Claims, thereby argues that such does not provide Novelty. Applicant believes that even in view of the overlap identified, the prior art does not suggest a Barrier that remains in place for "hours rather than minutes". The prior art does not suggest a time period of over about an hour. See Scott 493 Paragraph 0065 for instance where no time over "about an hour" is suggested. There are no teachings that a Barrier should remain in place between teeth and an oral environment for hours rather than minutes. Scott 493 even refers to the barrier referred to therein as temporary. See Paragraph 0035 therein.

The Examiner is also requested to consider that Scott et al. 493 recites the use of "Surfactant" in its composition of matter. See Scott et al. Claim 1. The presence of a Surfactant acts to reduce surface tension so there is no expectation of a Barrier formed thereby on teeth remaining in place for hours.

The Examiner is respectfully requested to consider said combination of supported Claim Requirements in this CIP at this time. In that light it is acknowledged that while cited references Thombre US2003/0175326 does not make any mention of a "barrier", both Scott et al. US2004/0101493 and Gergely et al. US2003/0206948 do use the word "barrier", but not at all in the context of the Present Application.

It is also noted that Scott (Published Application 2004/0101493) specifies its components "By Weight", whereas the Present Claims state "By Volume". And, Gangly (Published Application 2003/0206948) involves use of "Chewing Tablets".

In summary, it is believed that taken as a whole, the Claims as in this CIP are not remotely obviated by any cited single primary reference, and that no cited single primary reference provides one skilled in the art instructions as how to identify elements therein while rejecting other elements therein, and guides one skilled in the art to seek out other references and select specific elements therein, while rejecting other elements therein, and then modify the selected elements and combine them as now Claimed. Even in view of KSR, simply because elements in an invention are known in arguably somehow similar forms and distributed in a plurality of prior art references, does not render a specific combination thereof, and series of steps in a method, obvious.

A need remains for a system and method which would enable application of a material to teeth and gums, which material remains in contact with, and adheres to, said teeth and gums for a period long enough to neutralize acids in dental plaque biofilm, inhibit plaque from adhering to teeth and gums, encourage removal of dental plaque, and form a barrier between the teeth and gums and the oral environment, which barrier preferably remains in place for days if not intentionally removed.

DISCLOSURE OF THE INVENTION

As presented in the Parent application Ser. No. 12/380,972, the present invention is a method of controlling plaque on teeth which comprises the basic steps of providing a container that contains a composition of matter which:
  adheres to teeth and serves as a barrier between teeth and gums, and the environment;
  inhibits plaque from adhering to teeth; and
  optionally dissolves and/or absorbs plaque.

Said system can further serve to neutralize acids and freshen breath.

Said system further comprises means for dispensing said composition of matter for application onto teeth, wherein said means for dispensing said matter being is selected from the group consisting of:
  a tube comprising means for dispensing said composition of matter onto teeth, said dispensing means comprising a means for causing said material to extend from said tube in a manner allowing it to be placed into contact with teeth;
  a tub of composition for application via fingers or the like;
  a means for spraying said composition of matter at teeth.

Said system dispensing said composition of matter can further comprise a means for self-application, such as providing the composition of matter in a chewable system.

Said method further involves causing said system to mediate application of said composition of matter to teeth such that it remains in place for a period of time, in a substantially undiluted form, sufficient to remove plaque.

Said method can be practiced on a human, or on any animal, but typical practice on animals will involve application to cat or dog teeth.

Said method can provide that the composition of matter is selected to comprise plaque inhibiting matter, (eg. beeswax and sodium or potassium bicarbonate), and the composition of matter can further comprise at least one selection from the group consisting of oils, fragrances, preservatives, flavoring, colorings, medicinals and decay inhibiting components. (It is noted also that Beeswax provides negative ions when warmed, and presence in a typical mammalian's mouth will cause the plaque inhibiting effect. Most other waxes are not known to do so).

The composition of matter, which:
  adheres to teeth and serves as a barrier between teeth and gums, and the environment;
  inhibits plaque from adhering to teeth; and
  optionally dissolves and/or absorbs plaque;
can be fabricated by a method comprising the steps of:
  a) providing an edible wax and heating it until it becomes a liquid;
  b) entering a component which serves to inhibit plaque from forming on teeth and causing it to become substantially uniformly distributed therewithin;
  c) cooling the result.

Said method can further involve adding at least one selection from the group consisting of one or more oils, fragrances, flavors, preservatives, colorings and medicinals before cooling in step c.

Said method can also include providing at least one component which absorbs, (eg. diminishes), toxins.

Said composition of matter can comprise beeswax in functional combination with a plaque inhibiting ingredient, and can be comprise, by volume, approximately:
  1/8 edible adherent matter, such as beeswax, (one part);
  5/8 oil (five parts); and
  2/8 plaque inhibiting matter such as sodium and/or potassium bicarbonate (two parts).

(It is noted that the 5/8 oil can include medicinals and/or other components and that, for instance, honey or a gum can be substituted for, or added to the 1/8 edible adherent matter).

The plaque inhibiting matter can be, but is not limited to, sodium or potassium bicarbonate, and white beeswax is a preferred as a non-limiting edible adherent material. A decay inhibiting composition of matter can be fluoride or a functionally similar material.

The step of providing an edible adherent matter component can involve providing at least one selection from the group consisting of:
  beeswax;
  honey;
  gum;
  lanolin;
  tallow;
  carnuba;
  candelilla;
  soy;
  ceresin;
  montan;
  paraffin;
  ethylenic polymers;
  chlorinated naphthalenes;
  Fisher-Tropsch wax;
  castor wax;
  glycowax;
  carnuba wax;
in combination with an edible oil. Oils which can be applied in practice of the methodology can be selected from, but are not limited by, the group consisting of:
Nut Oils:
  almond oil;
  cashew oil;
  hazelnut oil;
  macadamia oil;
  pecan oil;
  pistachio oil;
  walnut oil;
Other Edible Oils:
  coconut oil;
  corn oil;
  cottonseed oil;
  canola oil;
  olive oil;
  palm oil;
  peanut oil;
  safflower oil;
  sesame oil;
  soybean oil;
  sunflower oil;
  acia oil;
  blackcurrant oil;
  borage oil;
  evening primrose oil;
  amaranth oil;
  apricot oil;

argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
*perilla* seed oil;
pine seed oil;
poppyseed oil;
prune kernel oil;
pumpkinseed oil;
*quinoa* oil;
ramtil oil;
rice bran oil;
thistle oil;
wheat germ oil;
radish oil;
rapeseed oil.

Flavorings which can be applied in practice of the methodology can be selected from the group consisting of:
almond flavored;
beef flavored;
chicken flavored;
turkey;
lamb flavored;
fish;
liver;
egg;
dairy flavored;
mint;
orange.

Any flavor which a human or animal would not reject can be used.

The step of providing a plaque inhibiting ingredient can involve providing at least one selection from the group consisting of:
sodium bicarbonate;
potassium bicarbonate; and
other buffering salt;
and can involve providing a decay inhibiting matter component such as fluoride.

Said method can also involve the step of applying said composition of matter to said teeth via:
application from a stick of material;
application by use of finger;
application by use of an applicator held by fingers;
application via a spray;
application by syringe; and
application via applying a strip containing said material to said teeth;
application via use of an application brush or the like, as opposed to an toothbrush brush which serves to remove matter.

Said system dispensing said composition of matter can further comprise a means for mammal self-application, such as providing the matter in a chewable system.

Further, while actually counter to the focus of present invention, said method can further comprise, after some relatively long time period, (eg. hours as opposed to minutes), after application of said composition of matter to teeth and/or gums, the step of removing said composition of matter applied to said teeth and/or gums by an approach that results in removal of plaque removed from teeth along therewith. This can be accomplished by, for instance brushing or wiping. While prior art describes brushing with sodium bicarbonate, which acts as an abrasive agent, said prior art does not describe intentionally maintaining the sodium bicarbonate in contact with teeth and gums, in a substantially undiluted form, for hours and longer, before optional removal.

Also, it is noted that the methodology can further include providing medication in said composition of matter for entry to a mammal's system via oral mucosa.

The present invention, being very portable, can be conveniently utilized whenever desired.

Additional recitation in this Application provides that present Application presents claims to a method of reducing plaque on mammalian teeth in an oral environment that does not involve require, for instance, chewing gum or require mechanical abrasion or surfactant or polybutene, but rather functions by maintaining contact of a composition of matter with teeth such that a barrier is formed thereby between said teeth and said oral environment for a period of at least an hour, comprising the steps of:

a) providing a system comprising a container for a composition of matter, which composition of matter:
adheres to teeth and serves as a barrier between teeth, and the oral environment;
inhibits plaque from adhering to teeth; and
reduces and/or absorbs plaque on teeth when left in place for hours rather than minutes;
which composition of matter does not require an acid component and has a pH of at least 6.0.

Said method proceeds with:
b) fabricating a composition of matter meeting the requirements listed in step a) and placing said composition of matter into said container;
c) dispensing some of said composition of matter having the properties listed in step a) from said container therefore, and causing it to be applied to the teeth of a mammal such that a majority thereof adheres to and remains in place on said mammalian teeth for a period of time of at least one hour in an undiluted form;
such that adherence of new plaque is inhibited, and/or existing plaque is reduced and/or absorbed.

Said method is distinguished by the forming of, and presence of, said plaque preventing and/or reducing barrier between said teeth and said oral environment for hours rather than minutes, and the absence of any requirement for the use of chewing gum or mechanical abrasion or surfactant or polybutene.

Said method can further comprise a step d, said step d being selected from the group consisting of:
d) repeating step c) at last once a day for at least one week;
d) repeating step c) for at least two weeks;
d) repeating step c) at least twice a day;
d) involves repeating step c) at least twice a day for at least two weeks.
d) involves repeating step c) at least once a day for more than two weeks.

Said method can involve the composition of matter further comprising at least one selection from the group consisting of oils, medicinals, fragrances, flavoring, preservatives and colorings.

Said method can involve that the composition of material matter that:
adheres to teeth and serves as a barrier between teeth, and the oral environment;

inhibits plaque from adhering to teeth; and
reduces and/or absorbs plaque on teeth when left in place for hours rather than minutes;
is fabricated by a method comprising the steps of:
a) providing an edible adherent matter component and heating it until it becomes a liquid;
b) entering a matter component which serves to inhibit plaque from forming on teeth and causing it to become uniformly distributed therewithin;
c) cooling the result.

Said composition fabrication. method can which further involve adding at least one selection from the group consisting of one or more oils, medicinals, fragrances, preservatives and colorings before cooling in step.

Said method can provide that said composition of matter comprises, by total volume of the composition, approximately:
1/8 beeswax;
5/8 oil; and
2/8 plaque inhibiting sodium and/or potassium bicarbonate.

Said method can involve that said oil contains at least one medicinal.

Said fabrication method can involve, in the step of fabricating a composition of matter, providing beeswax in functional combination with at least one component that absorbs and/or diminishes toxins.

Said method can involve step b at least one adherent selected from the group consisting of:
beeswax;
honey;
gum;
lanolin;
tallow;
candelilla;
soy;
ceresin;
montan;
paraffin;
ethylenic polymers;
chlorinated naphthalenes;
Fisher-Tropsch;
castor wax;
glycowax;
carnuba wax;
in combination with an oil.

Said method can involve the oil comprising at least one selection from the group consisting of:
almond oil;
cashew-oil;
hazelnut oil;
macadamia oil;
pecan oil;
pistachio oil;
walnut oil;
coconut oil;
corn oil;
cottonseed oil;
canola oil;
olive oil;
palm-oil;
peanut oil;
safflower oil;
sesame oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
*perilla* seed oil;
pine seed oil;
poppyseed oil;
prune kernel oil;
pumpkinseed oil;
*quinoa* oil;
ramtil oil;
rice bran oil;
thistle oil;
wheat germ oil;
radish oil;
rapeseed oil.

Said method can involve a flavoring also being provided as part of the oil which comprises at least one selection from the group consisting of:
almond flavoring;
beef flavoring;
chicken flavoring;
turkey flavoring;
lamb flavoring;
fish flavoring;
liver flavored;
egg flavoring;
dairy flavoring;
mint;
orange.

Said method can involve the plaque inhibitor that inhibits plague from adhering to teeth and reduces existing plaque when left in place over an hour, consists of at least one selection from the group consisting of:
sodium bicarbonate;
potassium bicarbonate.

Said method can involve the step of dispensing said composition of matter to said teeth involves a selection from the group consisting of:
application from a stick of said composition of matter;
application by use of finger;
application by use of an applicator held by fingers;
application via a spray;
application by syringe;
application via applying a strip containing said matter to said teeth;
application via an application brush; and
a chewable system which contains said composition of matter.

Said method can further comprise the step of removing said composition of matter applied to said teeth, by an approach that results in removal of plaque dislodged from teeth along therewith for aesthetic purposes.

Said method can further provide that the step of dispensing said composition of matter to said teeth involves a selection from the group consisting of:
  application from a stick of said composition of matter;
  application by use of finger;
  application by use of an applicator held by fingers;
  application via a spray;
  application by syringe;
  application via applying a strip containing said matter to said teeth;
  application via an application brush; and
  a chewable system which contains said composition of matter.

Said method can involve that the mammalian teeth are a selection from the group consisting of:
  cat teeth;
  dog teeth; and
  human teeth.

Said method can involve that said composition of matter remains in contact with said teeth for a period sufficiently long to freshen breath, neutralize acids in dental plaque biofilm, inhibit plaque from adhering to teeth, encourage removal of dental plaque, and form a barrier between the teeth and gums, and the oral environment, and even absorb into gums.

Said method can involve said composition of matter further comprises medication.

Said method of composition fabrication can involve that said method further comprises, prior to step c, the addition of medicine thereto.

Said method can involve the composition of matter further comprises at least one selection from the group consisting of:
  acid neutralizing material;
  breath freshening material;
  at least one medicinal; and
  at least one decay inhibiting material.

Said method can involve the composition of matter is formulated to include at least one selection from the group consisting of:
  acid neutralizing material;
  breath freshening material;
  at least one medicinal; and
  at least one decay inhibiting material.

Another recitation of a present invention method of reducing plaque on mammalian teeth in an oral environment that does not involve require, for instance, chewing gum or require mechanical abrasion or surfactant or polybutene, but rather functions by maintaining contact of a composition of matter with teeth such that a barrier is formed thereby between said teeth and said oral environment for a period of at least an hour, provides that it comprises the steps of:
  a) providing a composition of matter comprising, by total volume, approximately:
    1/8 beeswax;
    5/8 oil; and
    2/8 plaque formation inhibiting sodium and/or potassium bicarbonate;
  which composition of matter does not require an acid component and presents with a pH of at least 6.0.
  which in use:
    as a result of the beeswax adhering to teeth, serves as a barrier between teeth and the oral environment;
    as a result of the sodium and/or potassium bicarbonate inhibits plaque from adhering to teeth; and
    reduces and/or absorbs plaque on teeth when left in place for at least one hour.

Said method continues with:
  b) causing said composition of matter to be applied to mammalian teeth such that a majority thereof remains in place in an undiluted form for a period of time of at least an hour, with the result being that new plaque is inhibited from forming on said teeth, and at least some existing plaque is caused to be absorbed thereinto;
  c) repeating step b) at last once a day for at least one week; such that production of new plaque is inhibited, and/or existing plaque is reduced and/or absorbed.

Said method is distinguished by the forming of, and presence of said plaque preventing and/or reducing barrier between said teeth and said oral environment for hours rather than minutes, and the absence of any requirement for the use of chewing gum or mechanical abrasion or surfactant.

Said method can involve the composition of matter being caused to remain in contact with said teeth for a period of many hours, and a significant amount of existing plaque accumulation on teeth is caused to be reduced and/or absorbed thereinto.

Yet another recitation of a present invention method of reducing plaque on mammalian teeth in an oral environment that functions by maintaining contact of a composition of matter with teeth such that a barrier is formed thereby between said teeth and said oral environment for a period of at least an hour, provides that it comprises the steps of:
  a) providing a composition of matter, which composition of matter that:
    adheres to teeth and serves as a barrier between teeth and the oral environment;
    inhibits plaque from adhering to teeth; and
    reduces plaque on teeth when left in place for hours rather than minutes;
  which composition of matter does not require an acid component and presents with a pH of at least 6.0.

Said method continues with:
  b) applying said composition of matter having the properties listed in step a) to the teeth of a mammal such that a majority thereof adheres to and remains in place on said mammalian teeth as a barrier between said teeth and oral environment for a period of time of at least one hour in an undiluted form;
  such that adherence of new plaque is inhibited, and existing plaque is reduced.

Said method is distinguished by the forming of, and presence of said plaque preventing and/or reducing barrier between said teeth and said oral environment for hours rather than minutes, and the absence of any requirement for, for instance, the use of chewing gum or mechanical abrasion or surfactant or polybutene.

Any present invention method can provide that the pH of the composition is at least 7.0.

Any present invention method can provide that not only is there no requirement for the use of chewing gum or mechanical abrasion or surfactant or polybutene, there is no use thereof made.

Any present invention method can involve at least some gum tissue associated with said teeth of said mammal is included within the barrier formed between said teeth and said oral environment. It is noted that a significant amount of gum tissue can actually be coated with present invention composition with beneficial results being provided thereby.

As the Parent 972 Application was held to be deficient in that it did not provide support for negative limitations in the claims, it is specifically stated at this point herein that the preferred embodiment of the present invention does not involve use of garlic, charcoal, zinc, zinc oxide, sodium percarbonate, brushes, abrasive agents for their abrasive properties, ice, hemoglobin, oxygen, glycerin, acetic acid, *citrus* acid, *vitis* acid, (no strong acid is involved in any formulation of the present invention), peanut oil, polybutene, chewing gum, surfactants, emulsifiers, triclosan, removable backing strips, toothpastes, chewable toys, polymers, hexametaphosphate, etc. These, and other extraneous materials or compositions of matter and practices are identified in various cited prior art. The present invention functions by providing a barrier between teeth and an oral environment for a period of at least an hour. Any material or compositions of matter or practice not required to cause said "barrier" effect and includes a plaque inhibiting and/or reducing or other agent which reduces adherence to teeth is not required by the present invention. Such exclusions as just exemplified are simply not present in the preferred embodiment of the present invention. Neither present in the present invention method is a requirement for removal of the barrier forming agent in the present invention, although optional removal can be practiced, at some time, for aesthetic purposes.

In the foregoing, wherein a barrier is stated to be formed, it is to be understood that said barrier can also involve at least some gum tissue associated with teeth of said mammal be included within the barrier formed between the teeth and said oral environment. It is noted that benefit results where as much gum tissue as it is possible to contain, is contained within said barrier.

The invention will be better understood by reference to Detailed Description Section of this Specification, in combination with the Drawings.

DETAILED DESCRIPTION

Figure 1:
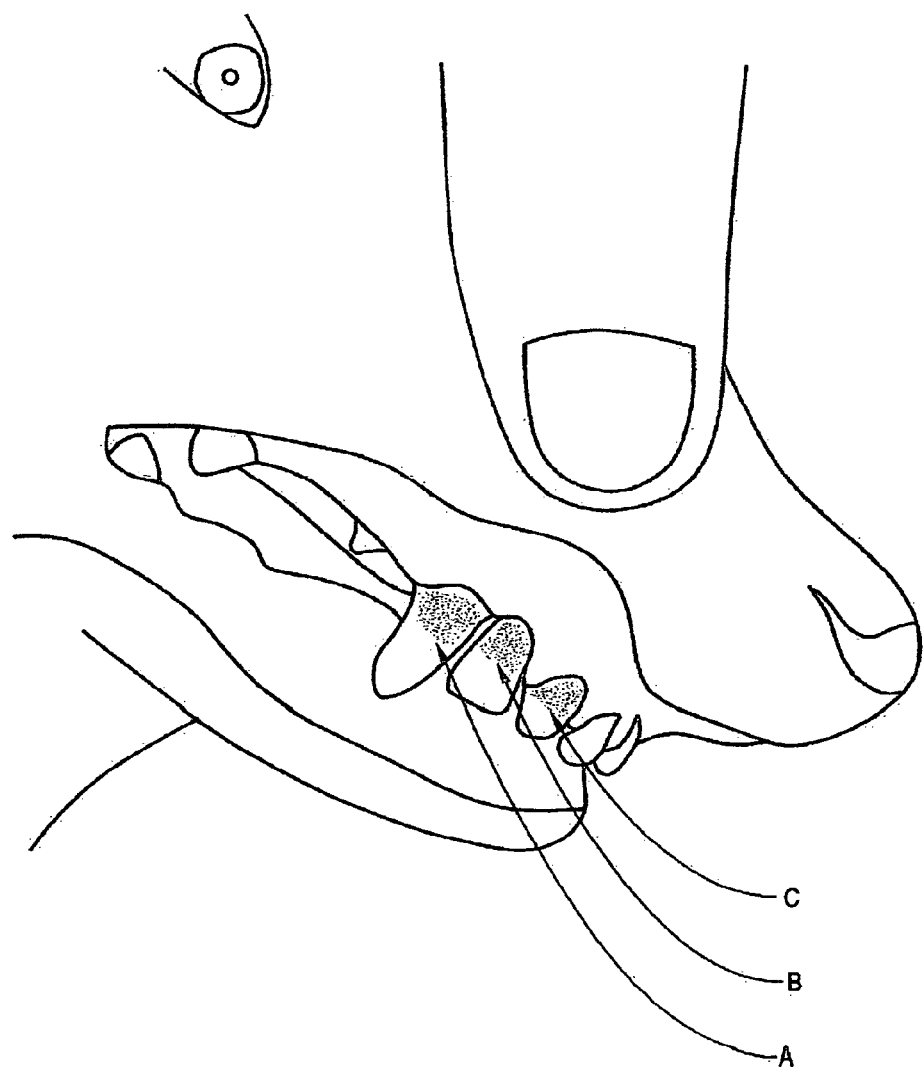
FIG. 1 shows a photo of a dog's teeth before application of a present invention composition of matter thereto.
Figure 2:
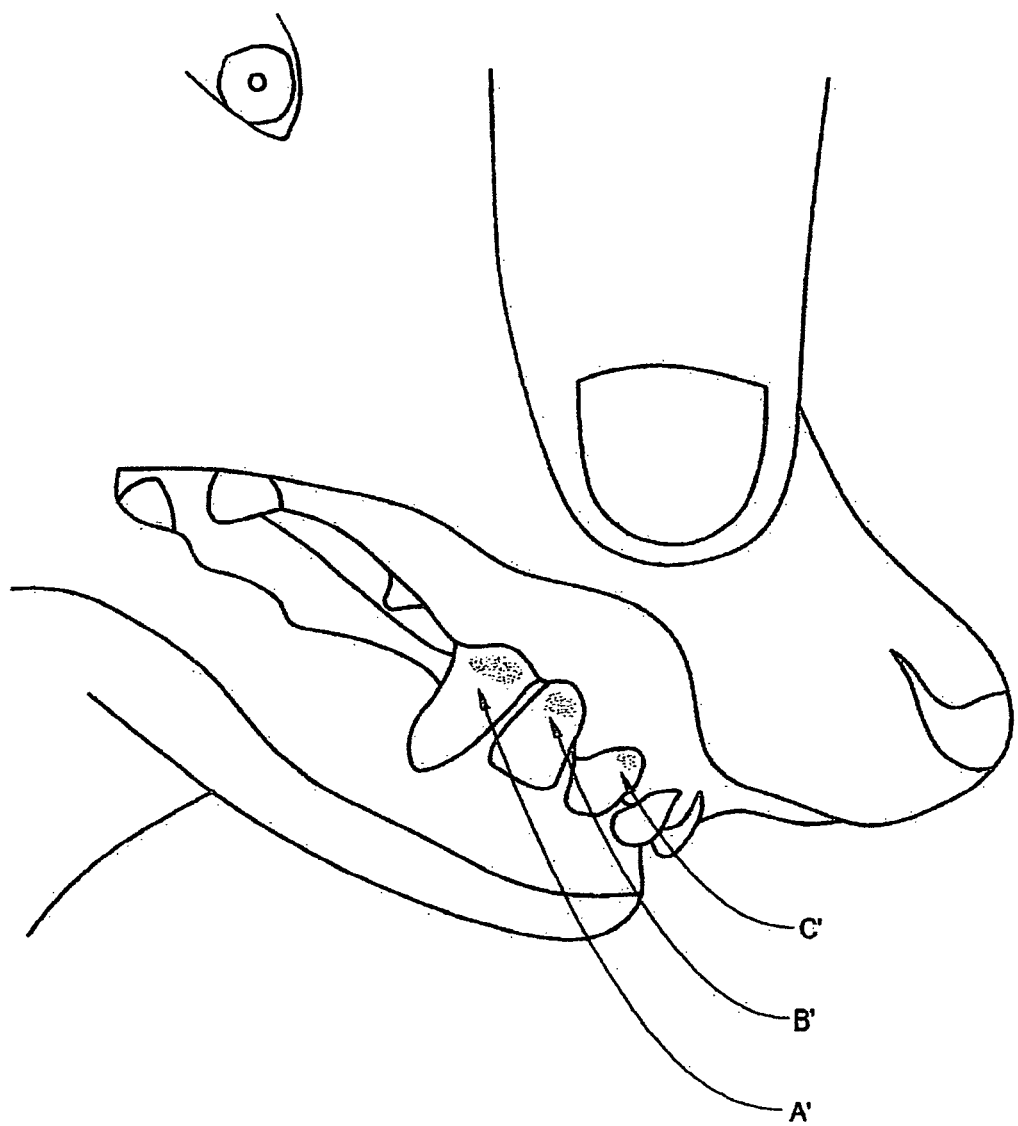
FIG. 2 shows a photo of a dog's teeth after use of a present invention composition of matter thereto over a period of two to three weeks.

Turning now to FIGS. 1 and 2, there are shown sketches based on photos of a dog's teeth before and after treatment by a present invention composition of matter thereto. The composition used was comprised of, by volume:
1/8 white beeswax;
5/8 almond oil, (which can include medicinals or other materials); and
2/8 sodium bicarbonate;
and was prepared by placing the beeswax and almond oil into a container in a water bath which was heated until said components thoroughly mixed with one another, and then the sodium bicarbonate was added and mixed until it was evenly distributed in the mix.
(Again, it is noted that the 5/8 oil can include medicinals and/or other components and that, for instance, honey or a gum can be substituted for, or added to the 1/8 white beeswax).

Application to the dog's teeth was accomplished by placing present invention composition on the applier's finger and transfer to the dog's teeth there via. Note that FIG. 2 shows that plaque present on the dog's teeth in FIG. 1 is reduced. The results depicted correspond to application once or twice a day over period of two to three weeks. The dog's breath was noted to improve in the first week of use.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of reducing plaque on mammalian teeth in an oral environment that does not comprise any selection from the group consisting of:
chewing gum;
mechanical abrasion;
surfactant;
polybutene;
a backing strip; and
a brush;
and which maintains contact with teeth such that a barrier is formed between said teeth and said oral environment for a period of at least an hour, comprising the steps of:
a) providing a container for said composition of matter, which composition of matter:
consists of, by total volume:
approximately 1/8 edible adherent matter;
approximately 5/8 oil; and
approximately 2/8 plaque inhibiting sodium and/or potassium bicarbonate; which
adheres to teeth and serves as a barrier between teeth and the oral environment;
inhibits plaque from adhering to teeth; and
reduces and/or absorbs plague on teeth when left in place for hours rather than minutes;
and which composition of matter does not comprise an acid component and has a pH of at least 6.0;
b) placing said composition of matter into said container, said composition of matter being fabricated by a method comprising the steps of:
a') providing said edible adherent matter and oil, and heating it until it becomes a liquid;
b') entering said sodium and/or potassium bicarbonate causing it to become uniformly distributed therewithin; and
c') cooling the result;
c) dispensing some of said composition of matter from said container, and applying it to the teeth of a mammal such that a majority thereof adheres to and remains in place on said mammalian teeth for a period of time of at least one hour.

2. A method as in claim 1 which further comprises a step d, said step d being selected from the group consisting of:
d) repeating step c) at least once a day for at least one week;
d) repeating step c) for at least two weeks;
d) repeating step c) at least twice a day;
d) repeating step c) at least twice a day for at least two weeks;
d) repeating step c) at least once a day for more than two weeks.

3. A method as in claim 1 in which the oil of said composition of matter further consists of at least one selection from the group consisting of oils, medicinals, fragrances, flavoring, preservatives and colorings.

4. A method as in claim 1, wherein the composition of matter further consists of at least one selection from the group consisting of medicinals, fragrances, preservatives and colorings being provided in step b'), before cooling the result.

5. A method as in claim 1 wherein said oil further consists of at least one medicinal.

6. A method as in claim 1 in which the edible material is beeswax and wherein the edible material further consists of:
at least one component which absorbs and/or diminishes toxins.

7. A method as in claim 1 in which the edible adherent material is at least one selection from the group consisting of:
beeswax;
honey;
gum;
lanolin;
tallow;
candelilla;
soy;
ceresin;
montan;
paraffin;
ethylenic polymers;
chlorinated naphthalenes;
Fisher-Tropsch wax;
castor wax;
glycowax; and
carnuba wax;
in combination with an oil.

8. A method as in claim 1 in which the oil in step a) is at least one selection from the group consisting of:
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
*perilla* seed oil;
pine seed oil;
poppyseed oil;
prune kernel oil;
pumpkinseed oil;
*quinoa* oil;
ramtil oil;
rice bran oil;
thistle oil;
wheat germ oil;
radish oil; and
rapeseed oil.

9. A method as in claim 1 wherein the composition of matter further consists of a flavoring that is provided before step c' and wherein the flavoring is at least one selection from the group consisting of:
almond flavoring;
beef flavoring;
chicken flavoring;
turkey flavoring;
lamb flavoring;
fish flavoring;
liver flavored;
egg flavoring;
dairy flavoring;
mint; and
orange.

10. A method as in claim 1 which further comprises the step of removing said composition of matter applied to said teeth which results in removal of plaque from teeth.

11. A method as in claim 1 in which
the step of dispensing said composition of matter to said teeth comprises a selection from the group consisting of:
application from a stick of said composition of matter;
application by use of finger;
application by use of an applicator held by fingers;
application via a spray; and
application by syringe.

12. A method as in claim 1 in which the mammalian teeth are a selection from the group consisting of:
cat teeth;
dog teeth; and
human teeth.

13. A method as in claim 1 wherein said composition of matter remains in contact with said teeth for a period sufficiently long to freshen breath, neutralize acids in dental plaque biofilm, inhibit plaque from adhering to teeth, encourage removal of dental plaque, and form a barrier between the teeth and the oral environment.

14. A method as in claim 1 wherein said composition of matter further consists of at least one medication.

15. A method as in claim 1 wherein, prior to step c', the composition of matter further consists of the addition of at least one medication thereto.

16. A method as in claim 1 in which the composition of matter further consists of at least one selection from the group consisting of:
acid neutralizing material;
breath freshening material;
at least one medicinal; and
at least one decay inhibiting material.

17. A method as in claim 1 in which the composition of matter is formulated to further consist of, by entering thereof before step c', at least one selection from the group consisting of:
acid neutralizing material;
breath freshening material;
at least one medicinal; and
at least one decay inhibiting material.

18. A method of reducing plaque on mammalian teeth in an oral environment that does not comprise any selection from the group consisting of:
   chewing gum;
   mechanical abrasion;
   surfactant;
   polybutene;
   a backing strip; and
   a brush;
but functions by maintaining contact of a composition of matter with teeth such that a barrier is formed between said teeth and said oral environment for a period of at least an hour, comprising the steps of:
   a) providing a composition of matter that consists of, by total volume, approximately:
   1/8 beeswax;
   5/8 oil; and
   2/8 plaque formation inhibiting sodium and/or potassium bicarbonate;
which composition of matter does not comprise an acid component and has a pH of at least 6.0;
which in use:
   as a result of the beeswax adhering to teeth, serves as a barrier between teeth and the oral environment;
   as a result of the sodium and/or potassium bicarbonate inhibits plaque from adhering to teeth; and
   reduces and/or absorbs plaque on teeth when left in place for at least one hour;
   b) applying said composition of matter to mammalian teeth such that a majority thereof remains in place for a period of time of at least an hour, with the result being that new plaque is inhibited from forming on said teeth, and at least some existing plague is caused to be absorbed thereinto;
   c) repeating step b) at least once a day for at least one week.

19. A method as in claim 1 in which the composition of matter is caused to remain in contact with said teeth for a period of many hours, and at least some of existing plague accumulation on teeth is caused to be reduced and/or absorbed thereinto.

20. A method as in claim 1, in which the pH is at least 7.0.

21. A method as in claim 18, in which the pH is at least 7.0.

22. A method as in claim 1, in which at least some gum tissue associated with said teeth of said mammal is included within the barrier formed between said teeth and said oral environment.

23. A method as in claim 18, in which at least some gum tissue associated with said teeth of said mammal is included within the barrier formed between said teeth and said oral environment.

24. A method as in claim 1 in which the composition of matter in step a) is applied to said teeth of a mammal and remains in place on said mammalian teeth as a barrier between said teeth and oral environment for a period of time of at least one hour in an undiluted form.

25. A method as in claim 18 in which the composition of matter in step a) is applied to said teeth of a mammal and remains in place on said mammalian teeth as a barrier between said teeth and oral environment for a period of time of at least one hour in an undiluted form.

26. A method of reducing plaque on mammalian teeth in an oral environment, comprising the steps of:
   a) providing a composition of matter, which composition of matter consists of approximately:
   1/8 edible adherent material;
   5/8 oil; and
   2/8 plaque formation inhibiting material;
      adheres to teeth and serves as a barrier between teeth and the oral environment;
      inhibits plaque from adhering to teeth; and
      reduces plaque on teeth when left in place for hours rather than minutes;
   and which composition of matter does not comprise an acid component and has a pH of at least 6.0; and
   b) applying said composition of matter in step a) to the teeth of a mammal such that a majority thereof adheres to and remains in place on said mammalian teeth as a barrier between said teeth and oral environment for a period of time of at least one hour;
such that adherence of new plaque is inhibited, and/or existing plaque is reduced;
said method being characterized by the forming of, and presence of said plaque inhibiting and/or reducing barrier between said teeth and said oral environment for hours rather than minutes, and does not require use of any selection from the group consisting of:
   chewing gum;
   mechanical abrasion;
   surfactant;
   polybutene;
   a backing strip; and
   a brush.

27. A method as in claim 26, in which:
said 1/8 edible adherent material component consists of at least one selection from the group consisting of:
   beeswax;
   honey;
   gum;
   lanolin;
   tallow;
   candelilla;
   soy;
   ceresin;
   montan;
   paraffin;
   ethylenic polymers;
   chlorinated naphthalenes;
   Fisher-Tropsch wax;
   castor wax;
   glycowax; and
   carnuba wax; and
said 5/8 oil component consists of at least one selection from the group consisting of:
   almond oil;
   cashew oil;
   hazelnut oil;
   macadamia oil;
   pecan oil;
   pistachio oil;
   walnut oil;
   coconut oil;
   corn oil;
   cottonseed oil;
   canola oil;
   olive oil;
   palm oil;
   peanut oil;
   safflower oil;
   sesame oil;
   soybean oil;
   sunflower oil;
   acia oil;

blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
*perilla* seed oil;
pine seed oil;
poppyseed oil;
prune kernel oil;
pumpkinseed oil;
*quinoa* oil;
ramtil oil;
rice bran oil;
thistle oil;
wheat germ oil;
radish oil; and
rapeseed oil; and
said 2/8 plaque formation inhibiting material consists of at least one selection form the group consisting of:
sodium bicarbonate; and
potassium bicarbonate.

28. A method of reducing plaque on mammalian teeth in an oral environment comprising:
a) providing a composition of matter that does not comprise any selection from the group consisting of:
chewing gum;
mechanical abrasion;
surfactant;
polybutene;
a backing strip; and
a brush;
but consists of, by total volume, a composition of matter consisting of approximately:
1/8 edible adherent material;
5/8 oil;
2/8 plaque inhibiting sodium and/or potassium bicarbonate;
said composition of matter further consisting of at least one selection from the group consisting of:
medicinals;
fragrances;
flavoring;
preservatives;
colorings;
at least one component which absorbs and/or diminishes toxins;
almond flavoring;
beef flavoring;
chicken flavoring;
turkey flavoring;
lamb flavoring;
fish flavoring;
liver flavored;
egg flavoring;
dairy flavoring;
mint;
orange;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;
acia oil;
black currant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
*perilla* seed oil;
pine seed oil;
poppyseed oil;
prune kernel oil;
pumpkinseed oil;
*quinoa* oil;
ramtil oil;
rice bran oil;
thistle oil;
wheat germ oil;
radish oil; and
rapeseed oil;
beeswax;
honey;
gum;
lanolin;
tallow;
candelilla;
soy;
ceresin;
montan;
paraffin;
ethylenic polymers;
chlorinated naphthalenes;
Fisher-Tropsch wax;
castor wax;
glycowax; and
carnuba wax;

b) said method further comprising applying some of said composition of matter to teeth of a mammal such that a majority thereof adheres to and remains in place on said mammalian teeth as a barrier between said teeth and oral environment for a period of time of at least one hour;

such that adherence of new plaque is inhibited, and/or existing plague is reduced.

* * * * *